United States Patent [19]
Wagner

[11] Patent Number: 6,071,268
[45] Date of Patent: Jun. 6, 2000

[54] OSTOMY SKIN BARRIER ASSEMBLY, STOMA SEAL ASSEMBLY AND MATERIALS FOR USE IN STOMA SEALS

[76] Inventor: Neldon C. Wagner, 19615 SW. Cascadia, Aloha, Oreg. 97007

[21] Appl. No.: 09/087,601

[22] Filed: May 29, 1998

[51] Int. Cl.[7] .................................................. A61F 5/44
[52] U.S. Cl. .......................... 604/332; 604/338; 604/342
[58] Field of Search ........................... 604/332, 336–339, 604/341, 342, 345

[56] References Cited

U.S. PATENT DOCUMENTS

| | | | |
|---|---|---|---|
| 2,971,510 | 2/1961 | Berger | 604/342 |
| 3,713,445 | 1/1973 | Marsan | 604/336 |
| 3,878,847 | 4/1975 | Marsan . | |
| 4,219,023 | 8/1980 | Galindo | 604/344 |
| 4,222,923 | 9/1980 | Rhodes et al. | 260/31.8 |
| 4,292,972 | 10/1981 | Pawelchak et al. . | |
| 4,496,357 | 1/1985 | Osborn | 604/336 |
| 4,538,603 | 9/1985 | Pawelchak et al. . | |
| 4,551,490 | 11/1985 | Doyle et al. | 524/22 |
| 4,610,676 | 9/1986 | Schneider et al. | 604/339 |
| 4,610,677 | 9/1986 | Muhiuddin | 604/339 |
| 4,660,553 | 4/1987 | Naylor et al. | 602/46 |
| 4,834,731 | 5/1989 | Nowak et al. | 604/339 |
| 4,865,594 | 9/1989 | Thomas | 604/332 |
| 4,889,534 | 12/1989 | Mohiuddin et al. | 604/339 |
| 4,973,323 | 11/1990 | Kaczmarek et al. | 604/339 |
| 5,269,773 | 12/1993 | Vidal | 604/342 |
| 5,302,173 | 4/1994 | Steer | 604/338 |
| 5,492,943 | 2/1996 | Stempel | 523/111 |
| 5,702,522 | 12/1997 | Sakauchi et al. | 117/2 |
| 5,702,973 | 12/1997 | Mitani et al. | 437/57 |

FOREIGN PATENT DOCUMENTS 719111 10/1965 Canada .................................. 604/338

OTHER PUBLICATIONS

Marshall, Moving Forward: Guideliesn on Care and Recovery Following Ileostomy Surgery, HERC Publishing (1996).
Sur–Fit Flexible Skin Barrier, Convatec, Princeton NJ.
Living with an Ileostomy the Easy, Active Life Way, Convatec, Princeton NJ (Mar. 1992).

*Primary Examiner*—Mark O. Polutta
*Attorney, Agent, or Firm*—K. David Crockett, Esq.; Crockett & Crockett

[57] ABSTRACT

An improved ostomy face plate. The improved face plate includes a ring seal of silicons foam, a blotter ring disposed between the ring seal and the barrier seal, and an improved barrier seal compound with a low isobutylene content.

7 Claims, 5 Drawing Sheets

6,071,268

OSTOMY SKIN BARRIER ASSEMBLY, STOMA SEAL ASSEMBLY AND MATERIALS FOR USE IN STOMA SEALS

FIELD OF THE INVENTION

This invention relates to appliances for use with stomas.

BACKGROUND OF THE INVENTION

An ileostomy is a surgical procedure in which the small intestines are surgically rerouted to the outside of the body. People require an ileostomy when the large intestines or rectum are affected by injury of disease to the point where they can no longer function and must be removed. Conditions which require removal of the large intestine or rectum include ulcerative colitis, polyposis, and tumors. When a surgeon removes the large intestine or rectum from a patient, the surgeon must also make a new passageway for removal of waste from the body. The surgeon does this by connecting the end of the small intestine (or a portion of the large intestine) to the outside of the body, and creating an opening in the skin. The opening in the skin is call a stoma, and is usually located on the right side of the abdomen near the waist. Related surgical procedures include the colostomy, in which colon is surgically rerouted to a stoma on the body, and the urostomy, in which the urinary tract is rerouted to a stoma on the body. Each of these ostomy procedures requires similar post-operative hygiene and appliances.

After ileostomy surgery, patients are relieved from the painful conditions requiring the ileostomy. However, the patients must use special appliances and use special care to remove waste material from the body through the ileostomy and stoma. Patients must wear a pouch over the stoma to collect waste material. The pouch is connected to the stoma with a fluid connector and a barrier seal around the stoma. The barrier seal may be is glued to the body around the stoma with special adhesive. The barrier seal is absorbent so that is absorbs any leakage that might occur through the fluid connector. The appliance may be disposable, in which case the pouch, fluid connector, and barrier seal are replaced as necessary. The appliance may be reusable, in which case the pouch must be emptied often, the fluid connector must be cleaned and reinstalled, and the barrier seal must be cleaned or replaced. The barrier seal must be replaced every two or three days. With proper vigilance to the hygiene requirements of the appliances, irritation of the stoma and skin around the stoma can be limited and odor associated with leakage can be avoided. With these special appliances, patients can engage in a very normal lifestyle, except for the time necessary to maintain the appliances and care for the stoma and experience of discomfort attendant to typical shortcomings of available appliances. The hygienic regimen is, however, burdensome and imperfect in avoiding irritation. Any device or method that lessens the burden on the patient and reduces the irritation of the stoma and surrounding skin will be useful for all ileostomy patients.

The stoma is a generally circular or annular opening in the abdomen. It is formed by piercing the skin to form a hole, pulling the ileum (the end of the small intestine) through the hole in the skin, and everting a short segment of the small intestine (turn it inside out), and suturing the everted segment to the skin. The sutures create a circle of stitches around the stoma. The stoma protrudes slightly from the surface of the skin, and the suture circle is slightly elevated.

The typical ileostomy pouch has a stoma opening which is aligned with the stoma, so that effluent flows from the small intestine through the stoma and stoma opening into the pouch. The pouch is held on the body, and stoma opening held in place over the stoma, with a faceplate that is taped to the body. The faceplate has a stoma opening which is ringed by a flanged fluid connector which connects to the stoma opening of the pouch. The stoma opening is the same size or slightly larger than the stoma, and may include a flexible silicone gasket with an opening the same size as the stoma. The faceplate is taped to the body with an adhesive disk call a barrier seal. The barrier seal is adhesive on both sides, and tapes the faceplate to the body. (The faceplate may also be glued to the body. Many patients also apply microporous tape around the faceplate before attaching the pouch to the faceplate, and some manufacturers supply the faceplate with a picture frame of tape.) The barrier seal is also absorbent, so that it absorbs any effluent that leaks from the stoma connection to the pouch. The pouch is fitted over the flange of the faceplate, and locked in place with a snap fit closure (like an aspirin bottle cap). This system is sometimes referred to as a two piece system, and may be described in various ways. For example, ConvaTec refers to the faceplate/barrier seal assembly as a skin barrier with a flange. The barrier seal is sometimes referred to as a skin seal, barrier ring seal, or wafer or disc.

In contrast to the two-piece system, a one piece system integrates the before mentioned components into one disposable unit who's overall function is similar to the two piece system. In another type of pouch, the stoma opening on the pouch has a tacky silicone ring which fits directly around the stoma, and the adhesive barrier seal connects the pouch directly to the skin around the stoma. Non-adhesive pouches use a similar setup, with an O-ring seal fitting around the stoma and the stoma opening of the pouch fitting directly over the O-ring, and the entire assembly is held on the body with a belt.

The integrity of the entire appliance depends on the effectiveness of the skin barrier seal. The barrier seal is intended to absorb effluent and keep it from contacting the skin around the stoma (referred to as the peristomal skin). When it fails in protecting the skin, the peristomal skin becomes irritated or infected. The skin barrier will not adhere to irritated or infected skin, and will not work to protect the skin. Thus any outbreak of peristomal skin irritation or infection can be very difficult to cure.

SUMMARY

The inventions described below include several improvements for ostomy appliances. The faceplate/barrier seal assembly includes a dispersive blotter ring installed between the faceplate and the barrier seal to distribute leaked effluent more evenly around the stoma opening, thereby prolonging the useful life of a barrier seal. The typical ring seal is improved by the addition of a highly conformal silicone foam ring. The silicone foam exhibits a balance of resilience and conformance beyond that of silicone ring seals, and expands into stoma concavities and irregularities that would otherwise remain as leaks. The silicone foam ring is suspended over the stoma with a suspension membrane which allows the foam ring to move and follow axial and radial displacements of the stoma relative to the faceplate. Addition of a superiorly located compressing and supporting ring assists in urging the silicone foam ring into contact with the stoma at its base. The faceplate assembly provides better protection to peristomal skin and prevents leaks better than currently available faceplate assemblies. A method of making silicone foam without use of bio-incompatible constituents or processing substances is also prevented, so that the device may be made without fear of harm to the body due to chronic exposure to chemicals diffusing from the ring seal.

DETAILED DESCRIPTION OF THE INVENTION

Figure 1:
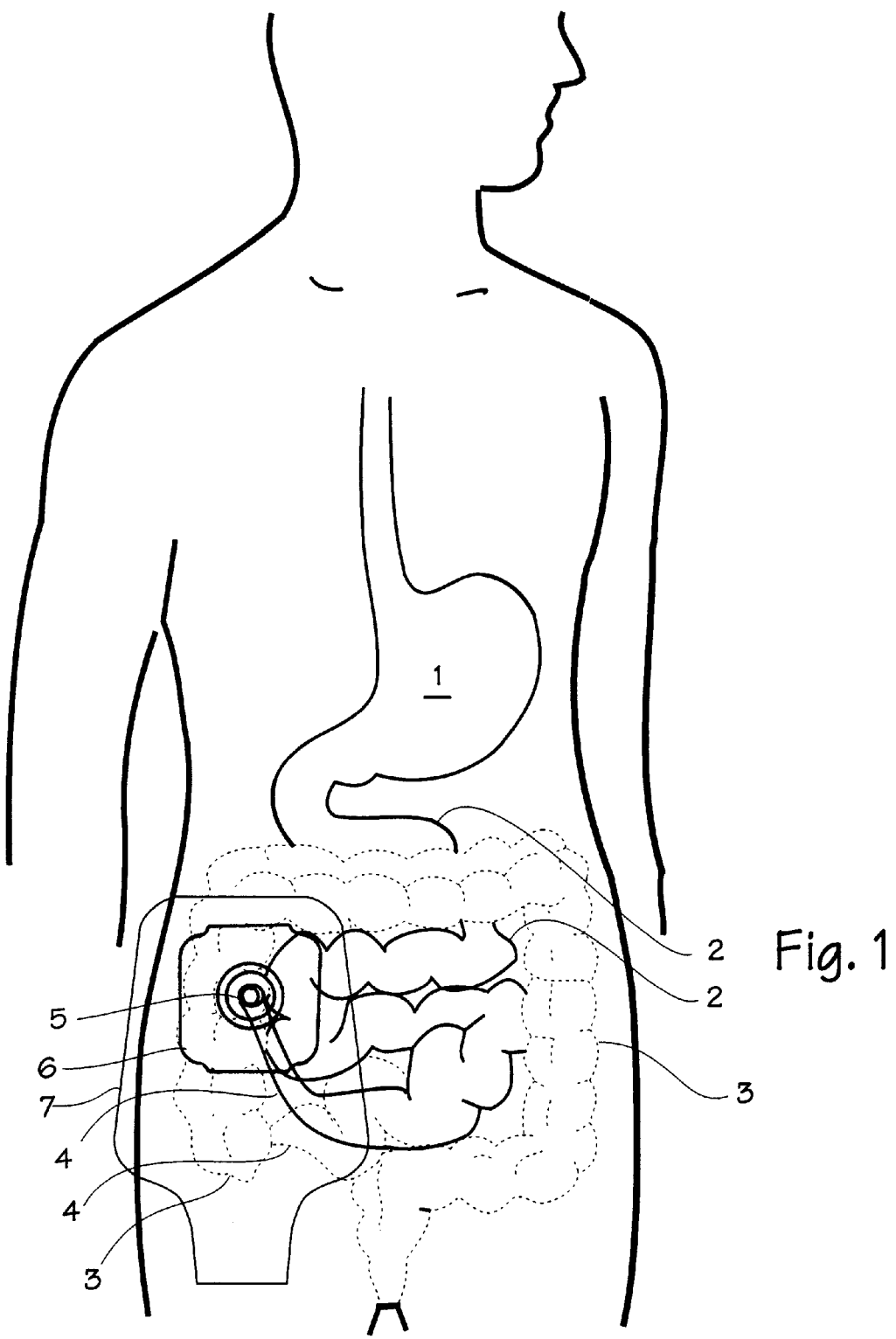
FIG. 1 is an illustration of the application of the flange in an ileostomy system.

FIG. 1 shows an overview of the installation of the ostomy faceplate and coupling system. The ileostomy is used to illustrate the invention. The normal pathway of nutrients through the digestive system includes the stomach 1, which discharges pre-digested sustenance to the small intestines 2. The small intestines terminate and communicate with the large intestine 3 (also called the colon). The distal portion of the small intestine which connects to the large intestine is referred to as the ileum 4, as is illustrated in phantom in its natural condition, and illustrated in the re-routed ileostomy position in solid lines. When the ileostomy is performed, the ileum is divided through, severing the small intestine from the large intestine. The cut end of the ileum is inserted in a hole in the abdomen to form a stoma 5. (The large intestine may be removed, except in occasional cases where the ostomy is intended to be temporary and the large intestine is still in useful or repairable condition, where the cut end of the large intestine is surgically closed.) The faceplate 6 is installed over the stoma, and the pouch 7 is snap-locked onto the faceplate.

Figure 2:
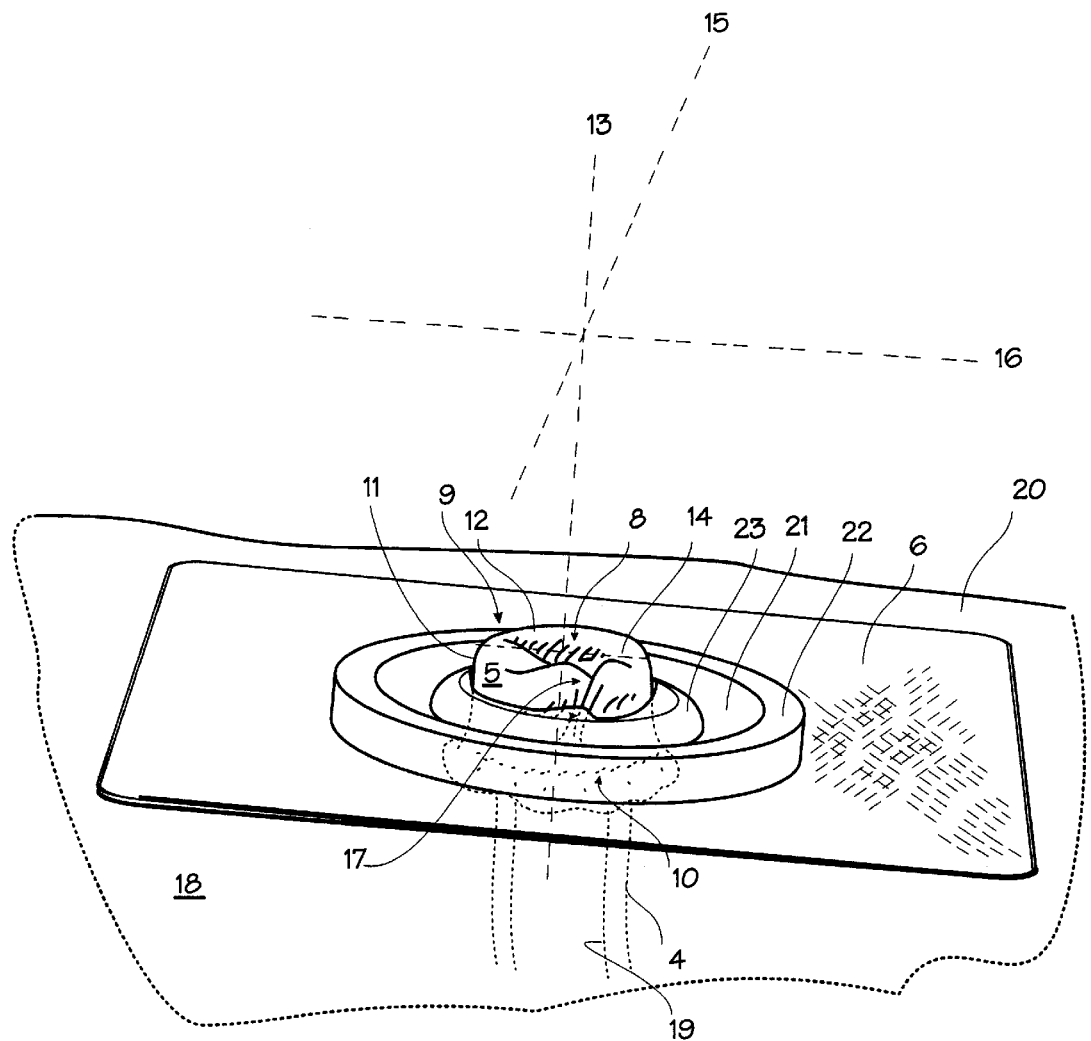
FIG. 2 illustrates the anatomy of a stoma and the structure of the flange in an application of the flange.

FIG. 2 shows the faceplate and stoma in more detail. The stoma 5 has been installed, and is defined by the ileum 4, ileum lumen 8, the everted or out-turned distal portion 9, and the sutured edge 10. The stoma typically has side walls 11 and a rim 12 which protrudes slightly from the abdomen. To aid in understanding the arrangement of the various parts of the faceplate, line 13 indicates the axis of the stoma and the ileum. Movement or placement of components along this line is referred to as axial movement, and positions close to the body along this line are referred to as posterior, and positions farther away from body along this line are referred to as anterior. Line 14 defines a radius of the stoma and stoma opening, and movement away from or toward this line is referred to as radial movement. Lines 15 and 16 indicates define the plane of the abdomen, and movement of the stoma and faceplate components around this plane is referred to as planar movement. Movement along line 15 and line 16 are referred to as vertical and lateral movement, or planar movement. The stoma will move relative to the faceplate along each of these lines during normal activities.

Stomas are generally symmetrical about the lumen of the ileum, but may certain areas of concavity 17 due to the natural anatomy of the small intestine or an asymmetric healing process. The stoma 5 is surrounding by normal abdominal skin, referred to as the peristomal skin and marked as item 18. The mucosal lining 19 of the ileum is exposed on the walls and rim of the stoma. The faceplate is mounted on the abdomen 20. The ring seal 21 is mounted on the faceplate, and includes a stoma opening. The pouch coupling ring 22 is secured to the faceplate and serves to couple the pouch of the faceplate with a snap-lock fitting. The inner edge of the stoma opening includes and is defined by a large bead 23 of silicone foam. The silicone foam is chosen because it is a material having a balance of resilience and conformance such that the bead will exert constant, light, radial pressure on stoma and rebound whenever pressed by movement of the stoma to maintain sealing contact with the stoma, yet will yield to protuberances in the stoma and expand into concavities in the stoma (as illustrated by the expansion of the ring seal into the concavity at 17). (Current ring seals are made of polyethylene film, which is not elastomeric, and are not capable of expanding into concavities, and patients must depend on sloppy stomahesive compound (like plumber's putty or dental adhesive) to fill gaps between the ring seal and the stoma. It also eventually dissolves and becomes ineffective as a gap filler.) The silicone foam may be an open celled foam or a closed cell foam. The silicone foam has an impermeable outer skin layer, but may be provided with a porous outer surface. A low modulus (that is, highly deflectable under load or deflectable under very low load), elastomer elastic material such as silicone foam used in the main seal provides a constant gentle sealing force around the stoma which is sufficient to provide a seal against leakage but slight enough to avoid stomach irritation.

Figure 3:
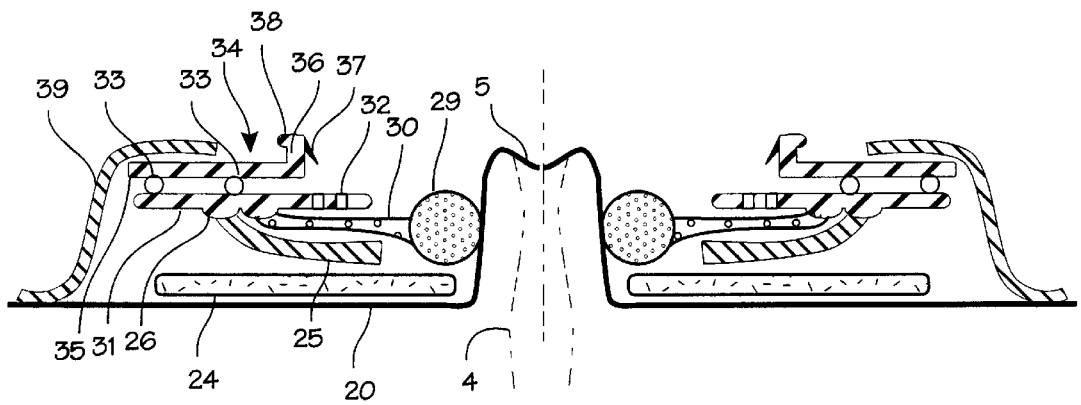
FIG. 3 is a cross section of an ostomy pouch faceplate.

FIG. 3 shows a cross section of the ostomy faceplate. The entire assembly is mounted on the abdomen 20, with the ileum 4 penetrating the abdomen to form the stoma 5. The faceplate assembly rests on the abdominal wall around the stoma. The barrier ring 24 comprises a compound of gelatin, pectin, polyisobutylene and glycerin. This barrier ring absorbs stoma mucus and expands as it absorbs mucus. It eventually liquifies to be expelled past the seal 29 into the pouch, or to be cleansed during maintenance and regular changing of the ostomy faceplate. (The barrier ring may be a conventional barrier ring, or it may be a barrier ring made of the new compound described below.) Immediately above the barrier ring, a blotter ring 25 is installed. The blotter ring blots up leaking liquid and disperses it around the circumference of the barrier ring, keeping liquid from pooling in any one portion of the barrier ring. This prevents non-uniform degradation or dissolution of the skin barrier ring, which is typically the cause of premature failure. The blotter ring is made from a porous material such as cloth, sponge, non-woven mat or other absorbent or wicking material which can distribute absorbed liquid uniformly over the circumference of the blotter ring. A few layers of polyester wipes sold under the tradename CHIX (Johnson & Johnson) tacked together with RTV silicone work well as blotter ring material. The blotter ring is fixed to the silicone support washer with an affixment of silicone 26 which may be formed of silicon glue (the affixment illustrated forms an annular boss around the bottom of the support membrane), or the blotter ring may be molded into the support washer during manufacture of the washer. The blotter ring may also be supplied as a replaceable structure, with blotter material fixed to a ring which snaps into a receiving groove on the support membrane.

In FIG. 3, the main sealing function of the faceplate is performed by the main seal ring 29. The main seal is toroidal, shaped like a donut, and is made of a low modulus foam encased in a flexible toroidal skin made of silicone or other flexible material. The inside diameter of the main seal ring is slightly smaller than the stoma diameter. It gently circumscribes the stoma and conforms to the outer contour of the stoma, and seals the stoma so that no effluent leaks past the main seal toward the barrier ring, blotter ring and peristomal skin. Thus, should the stoma outline have any concavity, the foam filled toroid is resilient and tensioned enough to expand into the concavity and followed any contour. The foam filled toroid is resilient enough to elastically follow movement of the stoma relative to the faceplate, and to follow the natural enlargement, shrinkage and deformation of the stoma that occurs during peristaltic actions (the natural squeezing of the intestines which forces stool outward) and daily activities. Contact with the stoma occurs over a relatively large surface area of the mucosal surface on the side wall of the stoma, and this minimizes stoma contact pressure and stoma irritation. An additional sealing enhancement occurs naturally by the continual supply of stoma mucosal secretion that acts like a filler and lubricating medium (like grease on an O-ring) that allows the main sealing ring to conform more effectively to the stoma surface, resulting in an enhanced seal.

The main seal 29 is supported by the seal suspension membrane 30. The seal suspension membrane is made of silicone or other very flexible and low modulus material, and may be secured to the main seal with a layer of dissolved silicone applied between the two (the dissolved silicone is painted on like glue). Besides affixing the main seal to the faceplate assembly, this seal suspension membrane isolates liquid on either side of the main seal. It supports the main seal as the main seal elastically follows the stoma as it changes shape, size and radial and planar position during its peristaltic maneuvers. Thus both the main seal and the main seal suspension membrane may resiliently move and deform in response to changes in stoma size and location to maintain a firm seal between the stoma and the main seal.

The main seal suspension membrane and the blotter ring are fixed to the silicone support membrane 31. The silicone support membrane is a relatively stiff membrane that fixes the seal suspension membrane and the main seal within the vicinity of the stoma, close to the abdomen and aligned axially within the elastic limits of the suspension membrane and the main seal. It keeps the main seal from drifting too far away from the abdomen and stoma. The closer the main seal is to the abdomen, the less stoma surface area is exposed behind the main seal, leaving less mucosal surface exposed to the skin barrier and therefore resulting is lower effluent load on the skin barrier. The support membrane is provided with relief holes 32 which pass from the lower side to the upper side of the membrane. These holes serve to allow any effluent trapped between the suspension membrane and the support membrane to pass through the support membrane into the ostomy pouch opening defined by the coupling ring. The support membrane lies underneath (posterior to) the pouch coupling ring and is attached to the pouch coupling ring with affixments 33. As illustrated, these affixments are beads of silicone glue. However, the pouch coupling ring may be attached to the support membrane with a simple layer of adhesive, or it may be made integral with the support membrane.

The pouch coupling ring 34 lies above (anterior to) the support membrane, and serves to couple the ostomy pouch with the faceplate. The coupling ring is made of tough slightly flexible plastic such as polyethylene, polypropylene or polystyrene. The base flange portion 35 rests on the support membrane 31, and the cylindrical ring 36 extends outwardly from the base flange. At the outward edge of the cylindrical ring, an internal flange 37 and external locking flange or lip 38 are integrally formed on the ring. These flanges interact with the receiving ring on the ostomy pouch to couple the pouch to the faceplate (one or the other, or both, may be provided in the coupling). The entire faceplate assembly is taped to the body with the tape 39, which is provided in the form of the circular picture frame tape. Commercial embodiments will probably include a peel away backing that is removed just prior to installation.

Figure 4:
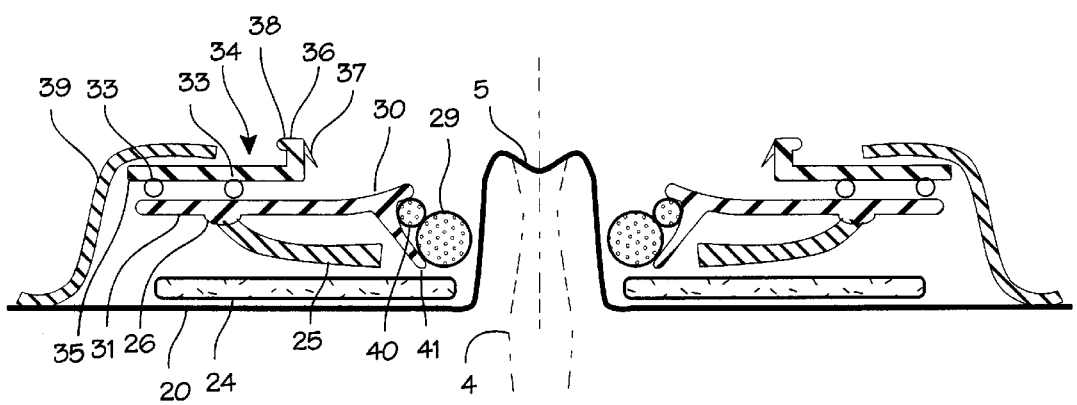
FIG. 4 is a cross section of an ostomy pouch faceplate.

FIG. 4 includes most of the elements of FIG. 3, with some additional features. A support ring 40 is provided under the inner circumference of the support membrane, trapped between the support membrane, the suspension strut 41 and the main seal. The purpose of this support ring is to gently urge the main seal downward, toward the abdomen, and allow the main seal to move more extensively in radial and planar directions relative to the support membrane. The main seal is suspended from the support membrane by any number of suspension struts 41, which extend downwardly from the support membrane. These suspension struts permit radial and planar movement and expansion of the support ring and main seal, but are biased against axial superior and inferior movement, thus prohibiting excessive movement of the main seal away from the abdomen. The struts also inhibit the entire structure of the main seal, compression ring and support membrane from everting outwards (i.e., turning inside out). The axial widths of the main seal, compression ring and struts are chosen such that the support membrane will slightly flex outward when the faceplate is installed (acting like an axial spring). This causes a gentle, constant inwards force that maintains the main seal position at the stoma base. The structure acts like a short, flexible tube, which bends to follow the stoma, but whose length remains relatively constant, keeping the seal close to the abdomen.

Figure 4A:
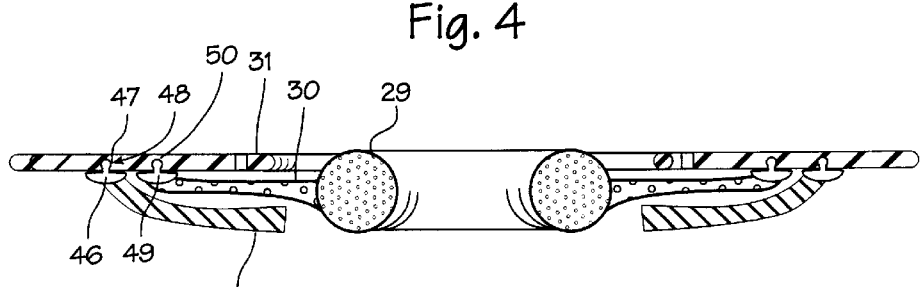
FIG. 4a is a cross section of a subassembly of the ostomy pouch.

As previously mentioned, the blotter ring may also be supplied as a replaceable structure. FIG. 4a illustrates an embodiment of the blotter ring, suspension membrane and support membrane assembly in which the blotter ring is mounted within a circular frame 46. The circular frame has a snap fit bead 47 around its anterior surface which fits into the snap fit groove 48 in the support membrane. Construction in this manner allows occasional change of the blotter ring without the need to change the other parts. The main seal suspension membrane can also be mounted on a circular frame 49 with an anterior snap fit bead 50 which fits into a snap fit groove on the support membrane.

Figure 5:
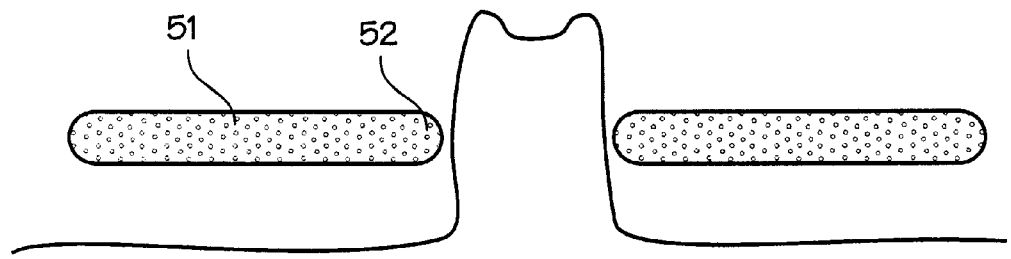
FIG. 5 illustrates an embodiment of the main seal.
Figure 6:
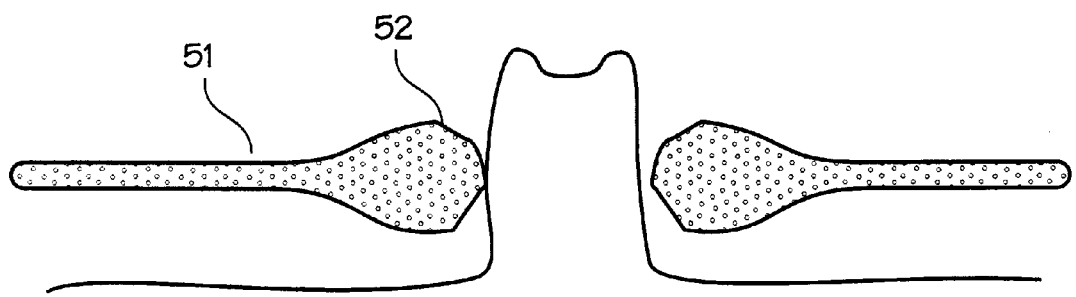
FIG. 6 illustrates an embodiment of the main seal.
Figure 7:
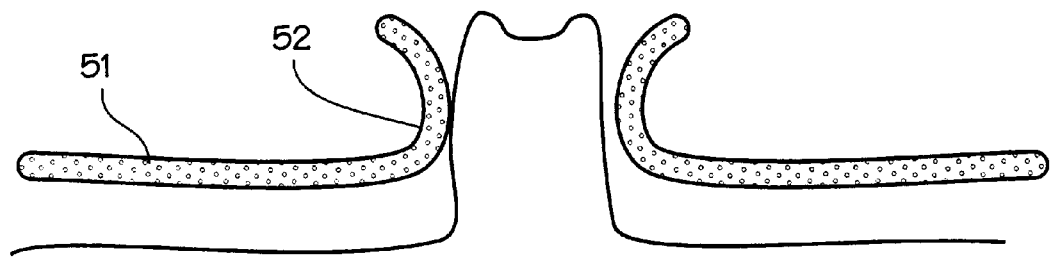
FIG. 7 illustrates an embodiment of the main seal.
Figure 8:
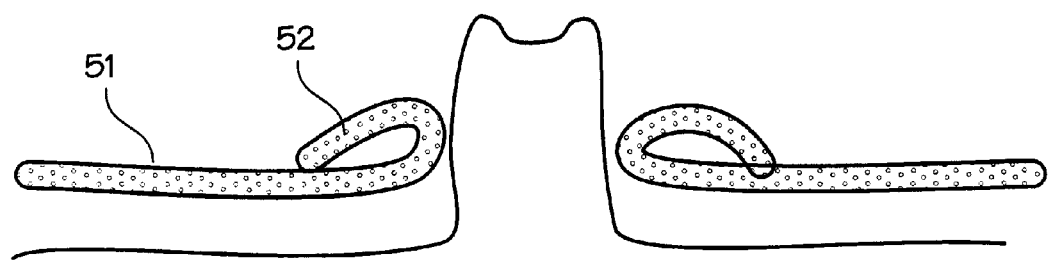
FIG. 8 illustrates an embodiment of the main seal.
Figure 9:
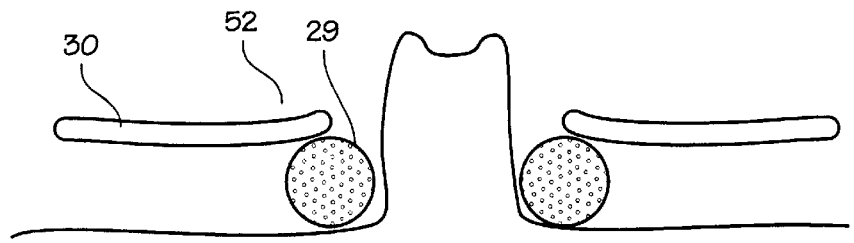
FIG. 9 illustrates an embodiment of the main seal.
Figure 10:
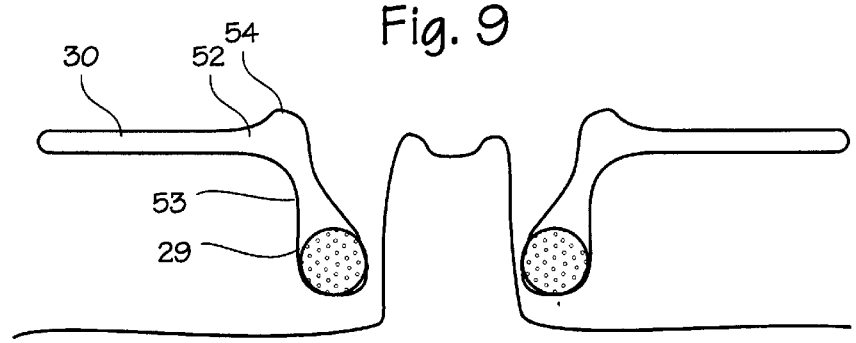
FIG. 10 illustrates an embodiment of the main seal.
Figure 11:
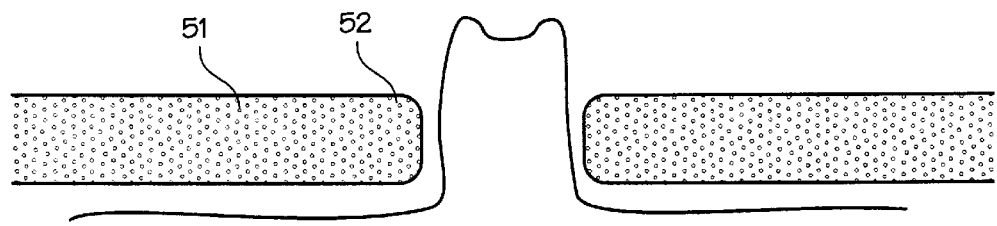
FIG. 11 illustrates an embodiment of the main seal.

Simpler embodiments of the main seal may be employed with the faceplate as constructed above. FIG. 5 illustrates an embodiment in which the main seal is a straight edged ring seal 51, where the inner edge 52 of the seal is not enlarged and is merely beveled with a round edge. FIG. 6 illustrates an embodiment in which the main seal is a ring seal 51 which has a bead of enlarged thickness around the inner edge 52 of the seal which defines the stoma opening. FIG. 7 illustrates an embodiment in which the main seal is a ring seal in which the inner edge of the seal is curled upward to define a rounded inner edge of the stoma opening. FIG. 8 illustrates an embodiment in which the main seal is a ring seal in which the inner edge of the seal is curled upward and hemmed to define a rounded inner edge of the stoma opening. The hem may be filled with air, foam, liquid or gel to enhance the resilience and conformance of the inner edge of the stoma. FIG. 9 illustrates an embodiment of the main seal in which the main seal is made of a ring seal in which a silicone foam ring 29 is mounted on the posterior side of the stoma opening of the suspension membrane 30. FIG. 10 illustrates an embodiment of the main seal in which the main seal is suspended from the suspension membrane 30 with an integrally formed resilient cylinder 53. This resilient cylinder is biased in the downward direction by the mass of the annular boss 54 on the inner edge 52 of the suspension membrane 30. FIG. 11 illustrates an embodiment of the main seal in which the main seal 29 is comprised solely of a flat washer of silicone foam secured directly to the faceplate and the pouch coupling ring 34. The main seal hole diameter is chosen to maximize sealing quality and minimize unnecessary stoma pressure. The preferred diameter is slightly smaller than the stoma diameter that, when applied, will result in a gentle squeezing of the stoma.

Figure 12:
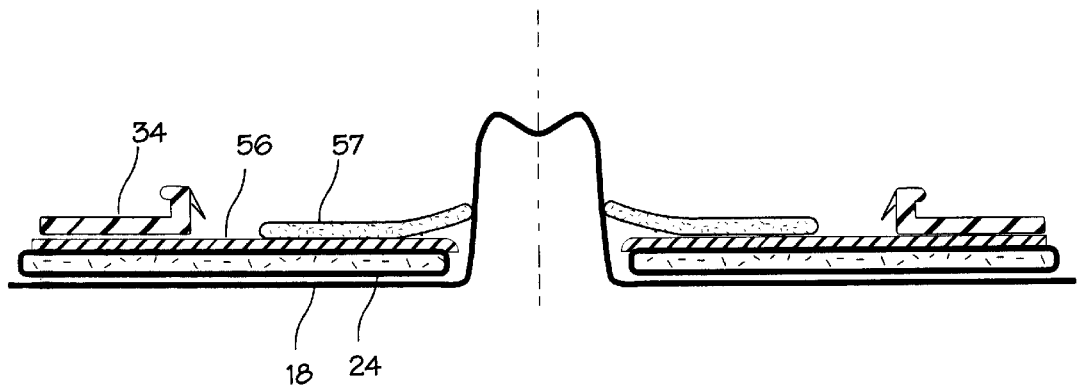
FIG. 12 illustrates an embodiment of the main seal.

FIG. 12 illustrates a simple improvement over commercially available faceplates. The skin barrier 24 lies immediately on the peristomal skin 18. The sealing ring is a multi-layered ring seal comprising a thin flange 56 made of polyethylene disposed over the skin barrier. The pouch coupling ring 34 is secured to the polyethylene layer. The polyethylene is nonelastomeric, and does not elastically yield when it moves relative to stoma. It also stretches under the force applied by the stoma, resulting in a loose seal between the ring and the stoma. (In the commercially available faceplate, the stoma hole is sized to bring the skin barrier 24 as close as possible to the stoma but limited minimally by the risk of irritating the stoma by having the plastic film too constrictive. The actual sealing mechanism is dependent upon the skin barrier compound to swell and expand around stoma, thereby inhibiting effluent from reaching peristomal skin.) To improve the sealing of the polyethylene ring seal, a thin layer of expanded PTFE 57 (expanded Teflon®, for example) or other elastomer, with an inside hole diameter that is smaller than the hole it augments, is secured to the polyethylene ring seal, forming a flexible membrane over the ring seal. The expanded PTFE is applied over or under the ring seal, and is secured with a thin layer of adhesive. This additional membrane forces the partially dissolved skin barrier 24 to form a larger, more robust "turtle neck" around the stoma (increasing surface area contact of skin barrier compound and stoma), that elastically follows any stoma motion. The sealing mechanism is now a combination of swelled skin barrier compound and the more positive seal of an elastomeric ring. In one embodiment of the main seal'application, especially when using a skin barrier compound that swells to form a "turtle neck, " the elastomeric main seal effectuates two primary functions, which can alternate in import depending upon the condition of the turtle neck formation. The first function, which has been previously described, depends upon contact of the main seal with stoma for the primary seal. The second function is to elastically circumscribe the "turtle neck" itself and urge it to follow any stoma motion. The swelled skin barrier compound acts like a thin intermediate layer of material between the stoma and main seal (like a thick layer of grease or an O-ring).

The ring seals of FIGS. 3 through 12 are made of very flexible and soft silicone which is formulated to enhance conformance to the stoma. Available silicone materials are generally unsuitable for use. RTV 5220 silicone has suitable elastomeric qualities of low modulus and good elasticity, and works well until it gets fagged out, but is not FDA approved. FDA approved silicones are not very flexible, and have relatively high modulus, and are resistant to deformation to a degree that is unsuitable for long term contact with the stoma. However, by cutting FDA approved silicone such as GE IS-802 with SF 18-350 silicone fluid (also referred to as silicone oil or polydimethylsiloxane), silicone can be formulated with a very low modulus.

The barrier seal described above may be made of conventional barrier seal compounds, which are typically made of a suspension of polyisobutylene, gelatin and pectin. These compounds are adhesive and absorbent. In other ostomy appliance applications, barrier seals made with these compounds are used as the main fastening element fastening the faceplate to the skin (the high tack characteristics to provide immediate protection to peristomal skin. The adhesive property is not critical in the embodiments of FIGS. 3 and 4 because the picture frame tape is sufficient to hold the device in place, and the main seal is more effective than other main seals. For these reasons, the proportion of polyisobutylene in the barrier seal compound used with these embodiment can be made very low.

The conventional barrier seal compound may be replaced with a new compound which has significantly longer life (it may be used for a week or more before requiring replacement). The new compound that has effective odor blocking characteristics, optimal tack, and is easier to clean up. The compound is a mixture of compounds mixed according to the following recipe: The components comprise 1.9 mm gelatin, 0.5 mm pectin, 0.5 gm carboxymethylcellulose (could use 'Poly-Grip'), 1.0 gm glycerin, 0–0.5 gm polyisobutylene and 6.0 gm water. The proportion of polyisobutylene can be minimized, even to zero.

The components are mixed and heated to near boiling until thick paste consistency. While hot, the mixture is poured onto a silicone covered release plate, and leveled to 0.1" thick (i.e. flattened with another release plate). The flat sheet of barrier seal material is cooled for about 10 minutes or more. After cooling, the sheet is dried at room temperature for about 36 hours (the release plates may be removed and the sheet may be placed on a drying screen). After drying, the sheet is ready for use and may be cut to convenient size, and the appropriate sized ostomy hole may be cut into the sheet. While this recipe works well for small batches, large production size batches will likely be made with methods more suitable to mass production. The amounts listed above indicate the desired proportions of the constituent compounds, and in production these proportions will most likely be expressed in reference to much larger amounts. However, the approximate proportions of 33.33 grams of polyisobutylene, 83.33 grams of carboxymethylcellulose, 83.33 grams of pectin, and 316.66 grams of gelatin per kilogram of water will provide the skin barrier of optimal tack and consistency, increased durability and easier cleanup. The proportion of polyisobutylene is extremely low compared to other skin barrier compounds, and may be varied in the range of zero to 100 grams per kilogram of water, and preferably within the range of 20–60 grams per kilogram of water. Finally, polyisobutylene may be left of the mix entirely. (Prior art systems have used high polyisobutylene content skin barrier compounds in order to provide high adhesive properties.) The skin barrier compound may be provided with additionally flexibility by the addition of a small amount of glycerin, in proportions of about 100–200 grams (preferably 170 grams) per kilogram of water.

In the embodiments which use foam as a constituent of the main seal, the foam may be made according to previously known methods of making silicone foam. However, the known methods are suspect for the inclusion of various bio-incompatible compounds or use of bio-incompatible compounds in their manufacture and subsequent leaching or evaporation out of the material and into contact with the body. To overcome the possibility of inclusion of such bio-incompatible compounds in the seal, the foam may be made in a new method which uses known biocompatible substances, namely silicone and water. In this new method, RTV silicone (plus any ingredients that alter its original modulus, i.e., silicone oil) is thoroughly mixed together with a solution of about 0.18 grams of water and 0.72 grams of acetone per gram of RTV silicone. The resultant paste is then pressed into a mold of appropriate shape, avoiding air entrapment. The paste is allowed to partially set at room temperature in the mold for approximately 10 to 15 minutes. After this brief period of setting, the mold and paste are heated in an oven for about ten hours or more at a temperature in the range of about 70 to 95° centigrade. The final foam density, pore size or bubble size, and resultant resilience of the foam is determined mainly by the curing temperature.

Many combinations and variations of temperature and cure time and proportions in the ingredients will provide foams of suitable resilience and conformance. A single combination may prove universally ideal with more extensive experience in clinical use. More likely, it will be best to provide a variety of foams of differing resilience and conformance for clinical use in order to suit the varying preference of individual patients. Many variations in the exact mix of water and acetone are suitable for making a silicone foam. Acetone may be replaced the composition with any substance which acts as a solvent for water and silicone.

Silicone has been mentioned as the material from which many components of the faceplate are made. This is because the biocompatability of silicone is well proven. Silicone can be made in formulations which exhibit a wide range of physical strength, flexibility, stiffness, and modulus. These formulations can be employed as indicated above. However, silicone is just one of many elastomers and plastics which can be used in the various components.

While the preferred embodiments of the devices and methods have been described in reference to the environment in which they were developed, they are merely illustrative of the principles of the inventions. It is specifically contemplated that new materials will be discovered to replace material currently preferred for use in the various parts of the faceplate, including the barrier skin seal, the main seal and the blotter ring. Other embodiments and configurations may be devised without departing from the spirit of the inventions and the scope of the appended claims.

I claim:

1. A device for attaching a stoma to a pouch, where said stoma is surrounded by peristomal skin, said device comprising:

a barrier ring having a posterior side intended for attachment to the peristomal skin and an anterior side facing away from the peristomal skin a ring seal disposed over the anterior side of the barrier ring, said ring seal having a stoma opening intended for placement over the stoma and axially aligned with the stoma;

a blotter ring disposed between the barrier ring and the ring seal, said blotter ring comprised of a porous material capable of absorbing stoma discharge; and a support washer disposed over the blotter ring and the ring seal, where the ring seal and blotter ring are fixed around their respective circumferences to the support washer.

2. The device of claim 1 further comprising a pouch coupling ring disposed over the support washer, said pouch coupling ring being attached to the support washer.

3. The device of claim 2 further comprising a frame of adhesive material securing the pouch coupling ring to the peristomal skin.

4. A device for attaching a stoma to a pouch, where said stoma is surrounded by peristomal skin, said device comprising:

a barrier ring having a posterior side intended for attachment to the peristomal skin and an anterior side facing away from the peristomal skin a ring seal disposed over the anterior side of the barrier ring, said ring seal having a stoma opening intended for placement over the stoma and axially aligned with the stoma;

a blotter ring disposed between the barrier ring and the ring seal, said blotter ring comprised of a porous material capable of absorbing stoma discharge;

wherein the ring seal comprises a silicone foam.

5. A device for attaching a stoma to a pouch, where said stoma is surrounded by peristomal skin, said device comprising:

a barrier ring having a posterior side intended for attachment to the peristomal skin and an anterior side facing away from the peristomal skin a ring seal disposed over the anterior side of the barrier ring, said ring seal having a stoma opening intended for placement over the stoma and axially aligned with the stoma;

a blotter ring disposed between the barrier ring and the ring seal, said blotter ring comprised of a porous material capable of absorbing stoma discharge;

wherein the ring seal comprises of low modulus, conformal elastomer.

6. A device for attaching a stoma to a pouch, where said stoma is surrounded by peristomal skin, said device comprising:

a barrier ring having a posterior side intended for attachment to the peristomal skin and an anterior side facing away from the peristomal skin a ring seal disposed over the anterior side of the barrier ring, said ring seal having a stoma opening intended for placement over the stoma and axially aligned with the stoma;

a blotter ring disposed between the barrier ring and the ring seal, and blotter ring comprises of a porous material capable of absorbing stoma discharge;

a pouch coupling ring adapted for releasable attachment to the pouch;

a ring seal suspension structure located posteriorly to the pouch coupling ring, said ring seal suspension structure connecting the pouch coupling ring to the ring seal;

wherein the ring seal suspension structure is comprised of a low modulus elastomer, and is capable of allowing the main seal to follow stoma motion.

7. The device of claim 6 wherein the ring seal suspension structure urges the main seal towards base of the stoma.

* * * * *